(12) United States Patent
Nakatsuka (10) Patent No.: US 9,746,416 B2
(45) Date of Patent: Aug. 29, 2017

(54) PHOTOACOUSTIC IMAGING APPARATUS

(71) Applicant: PreXion Corporation, Chiyoda-ku, Tokyo (JP)

(72) Inventor: Hitoshi Nakatsuka, Adachi-ku, Tokyo (JP)

(73) Assignee: PreXion Corporation, Tokyo (JP)

( * ) Notice: Subject to any disclaimer, the term of this patent is extended or adjusted under 35 U.S.C. 154(b) by 264 days.

(21) Appl. No.: 14/536,939

(22) Filed: Nov. 10, 2014

(65) Prior Publication Data

US 2015/0153269 A1 Jun. 4, 2015

(30) Foreign Application Priority Data

Nov. 29, 2013 (JP) .................................. 2013-247366

(51) Int. Cl.
A61B 5/00 (2006.01)
G01N 29/44 (2006.01)
G01N 21/17 (2006.01)

(52) U.S. Cl.
CPC ....... *G01N 21/1702* (2013.01); *A61B 5/0095* (2013.01); *G01N 29/44* (2013.01); *A61B 2560/0233* (2013.01); *G01N 2201/0621* (2013.01); *G01N 2291/01* (2013.01)

(58) Field of Classification Search
CPC .......... A61B 5/0095; A61B 2560/0233; G01N 21/1702; G01N 29/44; G01N 2201/0621; G01N 2291/01
USPC .......................................................... 73/643
See application file for complete search history.

(56) References Cited

U.S. PATENT DOCUMENTS

| | | | | |
|---|---|---|---|---|
| 3,522,580 A | * | 8/1970 | Lynch | G01H 5/00 367/95 |
| 5,437,178 A | * | 8/1995 | Esin | G01F 23/296 367/7 |
| 5,659,396 A | * | 8/1997 | Mondie | B65H 7/125 250/223 R |
| 2010/0191109 A1 | * | 7/2010 | Fukutani | A61B 5/0059 600/437 |
| 2011/0319743 A1 | * | 12/2011 | Satoh | A61B 5/0095 600/407 |
| 2012/0257472 A1 | * | 10/2012 | Yoda | A61B 5/0059 367/7 |
| 2012/0302866 A1 | * | 11/2012 | Fukutani | A61B 5/0095 600/407 |
| 2013/0302866 A1 | * | 11/2013 | Finley | C12N 9/0006 435/145 |
| 2014/0018659 A1 | | 1/2014 | Fukutani | |

FOREIGN PATENT DOCUMENTS

| | | |
|---|---|---|
| JP | 4611001 B2 | 1/2011 |
| JP | 2012-183295 A | 9/2012 |
| JP | 2012-217717 A | 11/2012 |
| JP | 2013-75000 A | 4/2013 |

* cited by examiner

*Primary Examiner* — J M Saint Surin
(74) *Attorney, Agent, or Firm* — Crowell & Moring LLP (57) ABSTRACT

A photoacoustic imaging apparatus includes a light source portion and a signal processing portion. The signal processing portion is configured to perform imaging processing on the basis of either a first acoustic wave signal or a second acoustic wave signal by performing processing for disabling either the first acoustic wave signal corresponding to a rising edge of a pulse signal of pulsed light or the second acoustic wave signal corresponding to a falling edge of the pulse signal of the pulsed light.

20 Claims, 4 Drawing Sheets

THIRD EMBODIMENT

PHOTOACOUSTIC IMAGING APPARATUS

BACKGROUND OF THE INVENTION

Field of the Invention

The present invention relates to a photoacoustic imaging apparatus, and more particularly, it relates to a photoacoustic imaging apparatus including a light source portion emitting light to a test object and a detecting portion detecting an acoustic wave generated from a detection target in the test object.

Description of the Background Art

A photoacoustic imaging apparatus or the like including a light source portion emitting light to a test object and a detecting portion detecting an acoustic wave generated from a detection target in the test object is known in general, as disclosed in Japanese Patent Laying-Open No. 2013-075000.

Japanese Patent Laying-Open No. 2013-075000 discloses a photoacoustic image generating apparatus (photoacoustic imaging apparatus) including a laser beam source emitting a pulsed laser beam to a test object and an ultrasonic probe (detecting portion) detecting a photoacoustic signal generated in the test object. In the photoacoustic image generating apparatus described in Japanese Patent Laying-Open No. 2013-075000, the laser beam source is employed as a light source, and hence the pulse width of the pulsed laser beam output from the laser beam source can be reduced.

When a light source other than the laser beam source is employed in the photoacoustic image generating apparatus described in Japanese Patent Laying-Open No. 2013-075000, however, it may be difficult to reduce the pulse width of the pulsed light output from the light source portion. In this case, a signal having accurate image information cannot be obtained, and hence the resolution is disadvantageously reduced.

SUMMARY OF THE INVENTION

The present invention has been proposed in order to solve the aforementioned problem, and an object of the present invention is to provide a photoacoustic imaging apparatus capable of suppressing a reduction in resolution even when it is difficult to reduce the pulse width of pulsed light.

In order to attain the aforementioned object, a photoacoustic imaging apparatus according to a first aspect of the present invention includes a light source portion emitting pulsed light to a test object and a signal processing portion performing imaging processing on the basis of either a first acoustic wave signal or a second acoustic wave signal by performing processing for disabling either the first acoustic wave signal generated from a detection target in the test object in correspondence to a rising edge of a pulse signal of the pulsed light or the second acoustic wave signal generated from the detection target in the test object in correspondence to a falling edge of the pulse signal of the pulsed light according to the pulsed light emitted by the light source portion.

In the photoacoustic imaging apparatus according to the first aspect of the present invention, as hereinabove described, the processing for disabling either the first acoustic wave signal generated from the detection target in the test object in correspondence to the rising edge of the pulse signal of the pulsed light or the second acoustic wave signal generated from the detection target in the test object in correspondence to the falling edge of the pulse signal of the pulsed light is performed. Thus, even in the case where the first acoustic wave signal and the second acoustic wave signal are generated while the peaks thereof are separated from each other by the pulse width when it is difficult to shorten the pulse width of the pulsed light, either the first acoustic wave signal or the second acoustic wave signal is disabled, whereby the first acoustic wave signal and the second acoustic wave signal are prevented from partially overlapping with each other and being recognized as one signal having a large width and are prevented from being misidentified as signals generated by different light detection targets. Thus, a reduction in resolution can be suppressed. Furthermore, the imaging processing is performed on the basis of either the first acoustic wave signal or the second acoustic wave signal, whereby the state of the inside of the test object can be faithfully reproduced as an image on the basis of the first acoustic wave signal or the second acoustic wave signal.

The aforementioned photoacoustic imaging apparatus according to the first aspect preferably further includes a detecting portion detecting the first acoustic wave signal and the second acoustic wave signal, and the signal processing portion is preferably configured to acquire the first acoustic wave signal and the second acoustic wave signal detected by the detecting portion and perform the imaging processing on the basis of either the first acoustic wave signal or the second acoustic wave signal by performing the processing for disabling either the first acoustic wave signal or the second acoustic wave signal which has been acquired. According to this structure, the first acoustic wave signal and the second acoustic wave signal detected by the detecting portion can be promptly processed by the signal processing portion.

In the aforementioned photoacoustic imaging apparatus according to the first aspect, the light source portion preferably includes an LED element emitting the pulsed light to the test object. According to this structure, the light source portion having the LED element capable of emitting the pulsed light to the test object is provided, whereby power consumption of the light source portion can be reduced unlike the case where a laser beam source is employed as the light source portion. In the case where the LED element is employed as a light source, it is currently difficult to shorten the pulse width of the pulsed light in view of the response speed of an LED and the characteristics of a switching element for pulse drive, and hence the present invention is particularly effective.

In the aforementioned photoacoustic imaging apparatus according to the first aspect, the light source portion preferably includes LED elements emitting the pulsed light having a first wavelength and a second wavelength different from each other to the test object, and the signal processing portion is preferably configured to acquire the first acoustic wave signal and the second acoustic wave signal with respect to each of the LED elements of the first wavelength and the second wavelength and perform the imaging processing on the basis of either the first acoustic wave signal or the second acoustic wave signal by performing the processing for disabling either the first acoustic wave signal or the second acoustic wave signal which has been acquired. According to this structure, using the LED elements of the first wavelength and the second wavelength different from each other, the state of each detection target in the test object can be faithfully reproduced as an image while the detection target is determined from the characteristics of the light absorptivity of the detection target according to the wavelength.

In this case, the signal processing portion is preferably configured to acquire the first acoustic wave signal and the second acoustic wave signal separately with respect to each of the LED elements of the first wavelength and the second wavelength by selecting the LED element of the second wavelength and causing the same to emit after selecting the LED element of the first wavelength and causing the same to emit. According to this structure, the first acoustic wave signal and the second acoustic wave signal can be acquired separately with respect to each of the LED elements of the first wavelength and the second wavelength. Consequently, signal processing on each of the LED elements of the first wavelength and the second wavelength can be easily performed.

In the aforementioned photoacoustic imaging apparatus according to the first aspect, the pulsed light emitted by the light source portion preferably has a prescribed pulse width, and the prescribed pulse width is preferably larger than a time obtained by dividing a detection distance desired by a user by the sound velocity. According to this structure, image information (acoustic wave signal) within the detection distance desired by the user can be included during a period from when the first acoustic wave signal is detected to when the second acoustic wave signal is detected. Therefore, even in the case where the second acoustic wave signal detected after the first acoustic wave signal is detected and thereafter a time corresponding to the prescribed pulse width elapses is disabled, for example, the reduction in resolution can be suppressed while the image information desired by the user is reliably acquired.

In the aforementioned photoacoustic imaging apparatus according to the first aspect, the pulsed light emitted by the light source portion preferably has a prescribed pulse width, and the signal processing portion is preferably configured to perform the imaging processing on the basis of the first acoustic wave signal by disabling the second acoustic wave signal detected after the first acoustic wave signal is detected and thereafter at least a time corresponding to the prescribed pulse width elapses. According to this structure, the second acoustic wave signal can be easily disabled, utilizing such a time lag of signal detection that after the first acoustic wave signal is detected according to the pulsed light emitted by the light source portion and the time corresponding to the prescribed pulse width elapses, the second acoustic wave signal is detected without any question.

In this case, the signal processing portion is preferably configured to perform signal processing for disabling the second acoustic wave signal during a prescribed period from immediately after elapse of the time corresponding to the prescribed pulse width until when subsequent pulsed light is emitted. According to this structure, the processing for disabling the second acoustic wave signal acquired in this time's detection period can be reliably terminated by the next time's acoustic wave detection period based on the next time's emission of the pulsed light.

In the aforementioned structure in which the imaging processing is performed on the basis of the first acoustic wave signal, in the pulsed light emitted by the light source portion, the rising edge where the first acoustic wave signal is generated preferably has an inclination equal to or more than the inclination of the falling edge where the second acoustic wave signal is generated. According to this structure, utilizing the property of the acoustic wave signal that the signal intensity of the acoustic wave signal corresponding to the edge of the pulse signal is increased as the inclination of the edge of the pulse signal is increased, the signal intensity of the first acoustic wave signal on which the processing for disabling a signal is not performed (which is enabled) can be easily increased.

In the aforementioned photoacoustic imaging apparatus according to the first aspect, in the pulsed light emitted by the light source portion, either the rising edge or the falling edge preferably has an inclination larger than the inclination of either the falling edge or the rising edge, and the signal processing portion is preferably configured to perform the imaging processing on the basis of either the first acoustic wave signal or the second acoustic wave signal by disabling the first acoustic wave signal or the second acoustic wave signal having signal intensity smaller than a prescribed threshold that is a value smaller than the signal intensity of the first acoustic wave signal or the second acoustic wave signal corresponding to either the rising edge or the falling edge. According to this structure, utilizing the property of the acoustic wave signal that the signal intensity of the acoustic wave signal corresponding to the edge of the pulse signal is increased as the inclination of the edge of the pulse signal is increased, the first acoustic wave signal and the second acoustic wave signal can be distinguished from each other with the prescribed threshold, and hence the first acoustic wave signal or the second acoustic wave signal can be reliably disabled.

In this case, in the pulsed light emitted by the light source portion, either the rising edge or the falling edge having the inclination larger than the inclination of either the falling edge or the rising edge preferably substantially vertically rises or falls. According to this structure, on either the rising edge or the falling edge where the enabled acoustic wave signal is generated, the inclination can be substantially maximized, and hence the intensity of the enabled signal can be reliably increased.

In the aforementioned structure in which the first acoustic wave signal or the second acoustic wave signal having the signal intensity smaller than the prescribed threshold is disabled, the prescribed threshold is preferably a value smaller than the signal intensity of the first acoustic wave signal or the second acoustic wave signal corresponding to either the rising edge or the falling edge and larger than the signal intensity of the second acoustic wave signal or the first acoustic wave signal corresponding to either the falling edge or the rising edge. According to this structure, the first acoustic wave signal and the second acoustic wave signal can be more reliably distinguished from each other with the prescribed threshold, and the first acoustic wave signal or the second acoustic wave signal can be more reliably disabled.

In the aforementioned photoacoustic imaging apparatus according to the first aspect, the pulse width of the pulsed light emitted by the light source portion is preferably at least 100 ns. According to this structure, a waveform in which the first acoustic wave signal and the second acoustic wave signal partially overlap with each other or a waveform in which the first acoustic wave signal and the second acoustic wave signal are separated from each other can be easily obtained, and hence the signal processing portion can easily perform the processing for disabling either the first acoustic wave signal or the second acoustic wave signal.

The aforementioned photoacoustic imaging apparatus according to the first aspect preferably further includes a detecting portion generating an ultrasonic wave to the test object, detecting the ultrasonic wave reflected by the test object, and detecting the first acoustic wave signal and the second acoustic wave signal, and the signal processing portion is preferably configured to perform the imaging processing on the basis of the ultrasonic wave detected by the detecting portion and either the first acoustic wave signal or the second acoustic wave signal. According to this structure, both an image by the ultrasonic wave and an image by the acoustic wave can be obtained, and hence the inside of the test object can be more finely reproduced as an image.

In the aforementioned photoacoustic imaging apparatus according to the first aspect, the light source portion preferably includes an LED element capable of emitting the pulsed light to the test object, a condensing lens condensing the pulsed light from the LED element, and a light guide portion guiding the pulsed light condensed by the condensing lens to the vicinity of the test object. According to this structure, even in the case where the LED element generating the light easily diffused (easily spread) as compared with a laser beam is employed as a light source, the light from the light source can be reliably emitted to the test object.

In the aforementioned photoacoustic imaging apparatus according to the first aspect, the signal processing portion is preferably configured to start to acquire the first acoustic wave signal and the second acoustic wave signal when the light source portion emits the pulsed light to the test object. According to this structure, the timing for emitting the pulsed light and the timing for acquiring the acoustic wave signal can be matched, and hence the acoustic wave signal according to the pulsed light can be easily acquired.

In the aforementioned photoacoustic imaging apparatus according to the first aspect, the light source portion is preferably configured to emit the pulsed light, which is near infrared light, to the test object. According to this structure, the near infrared light relatively difficult to absorb in the test object such as a human body, capable of reaching a deep portion of the test object, and suitable for measuring a human body or the like can be emitted, and hence the test object such as a human body can be easily measured.

A photoacoustic imaging apparatus according to a second aspect of the present invention includes a light source portion capable of emitting pulsed light to a test object such that the duty ratio is 50% and a signal processing portion separately acquiring a first acoustic wave signal generated from a detection target in the test object in correspondence to a rising edge of a pulse signal of the pulsed light and a second acoustic wave signal generated from the detection target in the test object in correspondence to a falling edge of the pulse signal of the pulsed light according to the pulsed light emitted by the light source portion and performing imaging processing on the basis of the first acoustic wave signal and the second acoustic wave signal which have been separately acquired.

In the photoacoustic imaging apparatus according to the second aspect of the present invention, as hereinabove described, the signal processing portion separately acquiring the first acoustic wave signal generated from the detection target in the test object in correspondence to the rising edge of the pulse signal of the pulsed light and the second acoustic wave signal generated from the detection target in the test object in correspondence to the falling edge of the pulse signal of the pulsed light and performing the imaging processing on the basis of the first acoustic wave signal and the second acoustic wave signal which have been separately acquired is provided. Thus, two pieces of image information (the first acoustic wave signal and the second acoustic wave signal) can be obtained from one pulse signal, and hence a double amount of image information (a double amount of sampling information) can be obtained as compared with the case where one piece of image information is obtained from one pulse signal.

In the aforementioned photoacoustic imaging apparatus according to the second aspect, in the pulsed light emitted by the light source portion, the inclination of the rising edge and the inclination of the falling edge are preferably substantially equal to each other in magnitude. According to this structure, the intensity of the first acoustic wave signal and the intensity of the second acoustic wave signal can be rendered substantially equal to each other, and hence the signal processing portion can easily perform the imaging processing based on the first acoustic wave signal and the second acoustic wave signal.

In the aforementioned photoacoustic imaging apparatus according to the second aspect, the pulsed light emitted by the light source portion preferably has a substantially rectangular shape. According to this structure, on both the rising edge and the falling edge, the inclination can be substantially maximized, and hence both the intensity of both the first acoustic wave signal and the second acoustic wave signal can be reliably increased.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Embodiments of the present invention are hereinafter described with reference to the drawings.

First Embodiment

The structure of a photoacoustic imaging apparatus 100 according to a first embodiment of the present invention is now described with reference to FIGS. 1 to 3.

Figure 1:
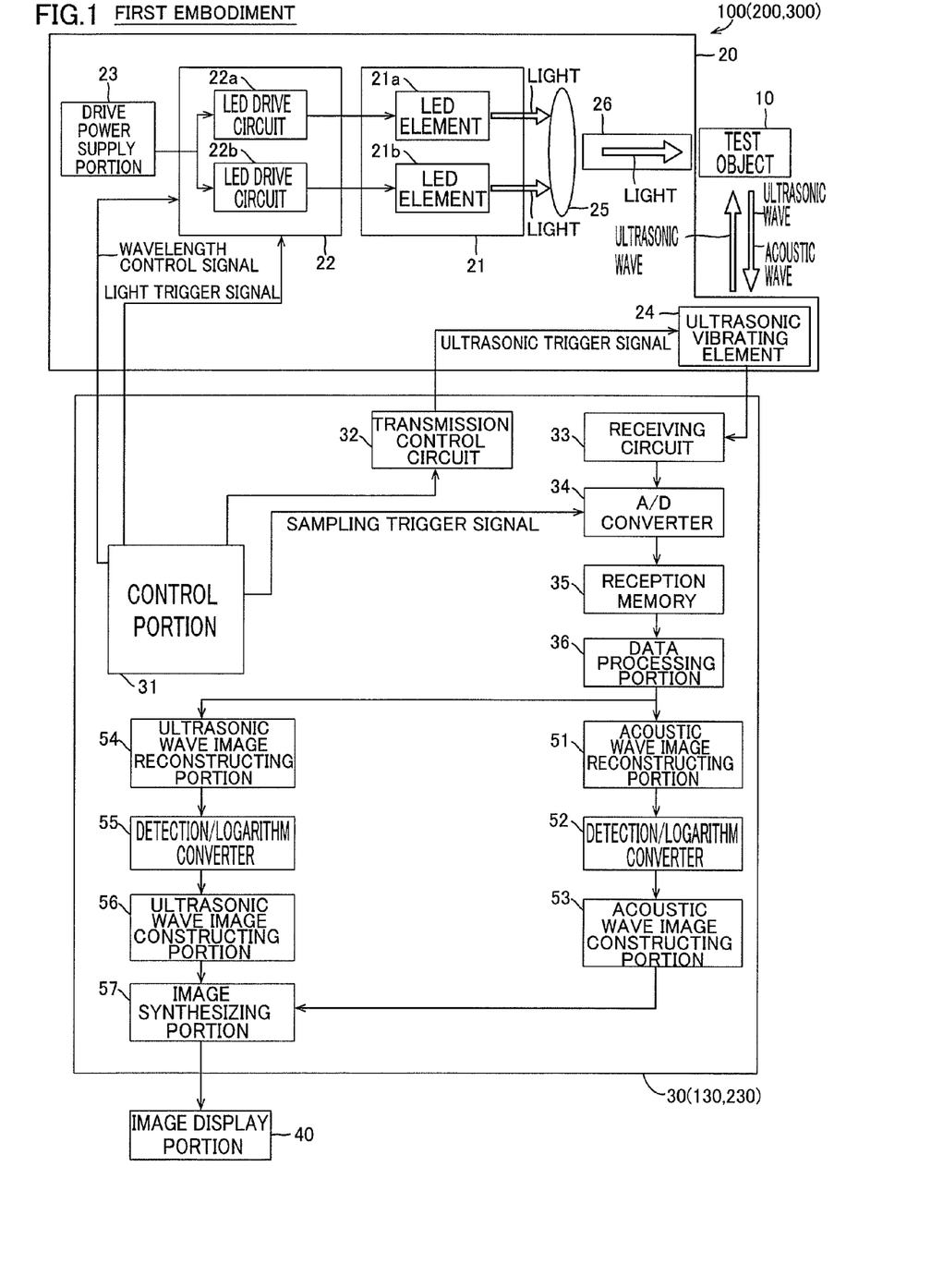
FIG. 1 is a block diagram showing the overall structure of a photoacoustic imaging apparatus according to a first embodiment of the present invention.

The photoacoustic imaging apparatus 100 according to the first embodiment of the present invention includes a detecting portion 20 configured to detect image information in a test object 10, a signal processing portion 30 processing and imaging a signal detected by the detecting portion 20, and an image display portion 40 configured to display an image processed by the signal processing portion 30, as shown in FIG. 1.

The detecting portion 20 includes a light source portion 21 emitting near infrared light to the test object 10, a light source drive circuit 22 transmitting a drive signal to the light source portion 21, and a drive power supply portion 23 supplying electric power to the light source portion 21 through the light source drive circuit 22. Furthermore, the detecting portion 20 includes an ultrasonic vibrating element 24 having a function of detecting an acoustic wave 70 (see FIG. 2) as an ultrasonic wave generated by absorption of the light by a light absorber 10a (see FIG. 2) in the test object 10 and a function of generating an ultrasonic wave 80 (see FIG. 2) to the test object 10 and detecting the ultrasonic wave 80 reflected by the test object 10. In addition, the detecting portion 20 includes a condensing lens 25 condensing the light from the light source portion 21 and a light guide portion 26 guiding the light condensed by the condensing lens 25 to the vicinity of the test object 10. In FIG. 1, only a set of the light source portion 21, the condensing lens 25, and the light guide portion 26 is shown for the convenience of illustration, but two sets of the aforementioned components are actually arranged in the detecting portion 20, as shown in FIG. 2. The light absorber 10a is an example of the "detection target" in the present invention.

In this description, the ultrasonic wave denotes an acoustic wave (elastic wave) having such a high frequency that a person with normal hearing does not have a sensation of hearing and an acoustic wave (elastic wave) of at least about 16000 Hz. In this description, the ultrasonic wave generated by the absorption of the light by the light absorber 10a in the test object 10 is distinguished as the "acoustic wave" from the ultrasonic wave generated by the ultrasonic vibrating element 24, reflected by the test object 10 as the "ultrasonic wave" for the convenience of description.

The light source portion 21 has an LED element 21a and an LED element 21b capable of emitting near infrared light having wavelengths different from each other.

The light source drive circuit 22 has an LED drive circuit 22a driving the LED element 21a and an LED drive circuit 22b driving the LED element 21b. The light source drive circuit 22 is configured to cause the LED element 21a to emit pulsed light through the LED drive circuit 22a and cause the LED element 21b to emit pulsed light through the LED drive circuit 22b.

Figure 2:
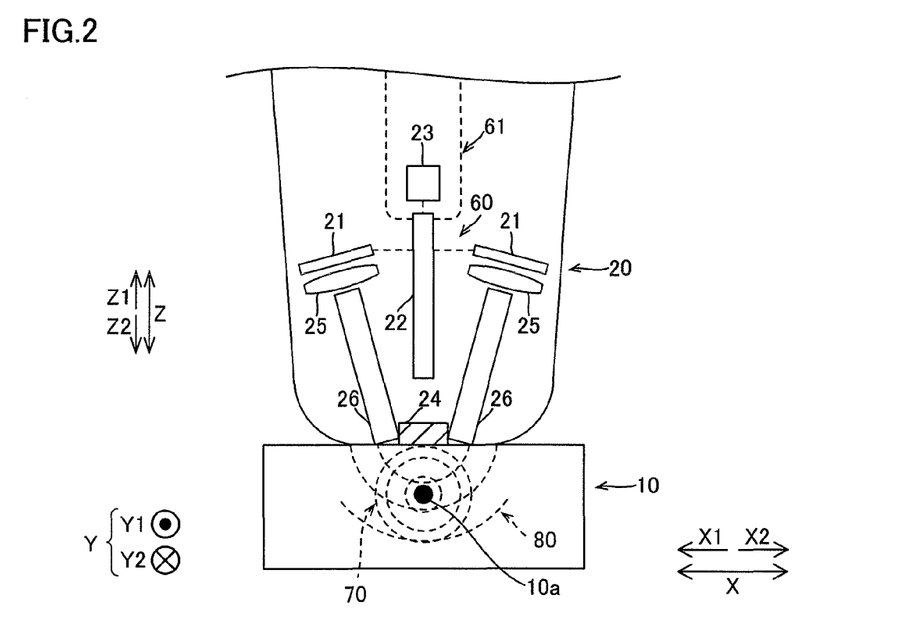
FIG. 2 illustrates a state of receiving an acoustic wave of the photoacoustic imaging apparatus according to the first embodiment of the present invention.

The detecting portion 20 is configured to detect the acoustic wave 70 generated from the light absorber 10a by emission of the pulsed light from the light source portion 21, as shown in FIG. 2. Furthermore, the detecting portion 20 is configured to detect the ultrasonic wave 80 emitted from the ultrasonic vibrating element 24 and reflected by the test object 10.

The detecting portion 20 includes two light source portions 21, two condensing lenses 25, and two light guide portions 26 (in pairs), and the aforementioned components in pairs are arranged to sandwich the ultrasonic vibrating element 24 therebetween. In the detecting portion 20, the light source drive circuit 22 and the drive power supply portion 23 are arranged between the two light source portions 21. In the detecting portion 20, the light source drive circuit 22 is arranged in the vicinity of the light source portions 21. The detecting portion 20 is configured such that the two light source portions 21, the light source drive circuit 22, and the drive power supply portion 23 are electrically connected to each other by electrical wires 60 (shown by broken lines) therein. Furthermore, the detecting portion 20 is configured such that the light source drive circuit 22 receives the signal from the signal processing portion 30 through a wire 61 (shown by a broken line).

The signal processing portion 30 includes a control portion 31 configured to control components of the signal processing portion 30 and the light source drive circuit 22, a transmission control circuit 32 transmitting an ultrasonic trigger signal to the ultrasonic vibrating element 24 on the basis of the control performed by the control portion 31, and a receiving circuit 33 configured to receive signals of the acoustic wave 70 and the ultrasonic wave 80 detected by the ultrasonic vibrating element 24, as shown in FIG. 1. The signal processing portion 30 further includes an A/D converter 34 converting the detected signals of the acoustic wave 70 and the ultrasonic wave 80 into digital signals, a reception memory 35 storing the detected signals of the acoustic wave 70 and the ultrasonic wave 80, and a data processing portion 36 processing the detected signal of the acoustic wave 70 and separating the detected signals of the acoustic wave 70 and the ultrasonic wave 80 from each other. The processing of the signal of the acoustic wave 70 is described later in detail.

The signal processing portion 30 further includes an acoustic wave image reconstructing portion 51 reconstructing the separated signal of the acoustic wave 70 as an image, a detection/logarithm converter 52 performing waveform processing upon output of the acoustic wave image reconstructing portion 51, and an acoustic wave image constructing portion 53 constructing a tomographic image in the test object 10 based on the detected signal of the acoustic wave 70. The signal processing portion 30 further includes an ultrasonic wave image reconstructing portion 54 reconstructing the signal of the ultrasonic wave 80 reflected from the test object 10 as an image, a detection/logarithm converter 55 performing waveform processing upon output of the ultrasonic wave image reconstructing portion 54, and an ultrasonic wave image constructing portion 56 constructing a tomographic image in the test object 10 based on the detected signal of the ultrasonic wave 80. The signal processing portion 30 further includes an image synthesizing portion 57 synthesizing the image constructed by the acoustic wave image constructing portion 53 and the image constructed by the ultrasonic wave image constructing portion 56 and is configured to output an image synthesized by the image synthesizing portion 57 to the image display portion 40.

The processing of the acoustic wave signal in the photoacoustic imaging apparatus 100 according to the first embodiment of the present invention is now described with reference to FIGS. 1 and 3.

First, a wavelength control signal is transmitted from the control portion 31 of the signal processing portion 30 to the light source drive circuit 22, as shown in FIG. 1. Then, the light source drive circuit 22 selects either the LED element 21a or the LED element 21b on the basis of the received wavelength control signal. Thereafter, a light trigger signal is transmitted from the control portion 31, and the light source drive circuit 22 receiving the light trigger signal transmits the drive signal (pulse signal) to the selected LED element 21a or LED element 21b. The LED element 21a or the LED element 21b receiving the drive signal (pulse signal) emits the pulsed light to the test object 10 through the condensing lens 25 and the light guide portion 26.

Figure 3:
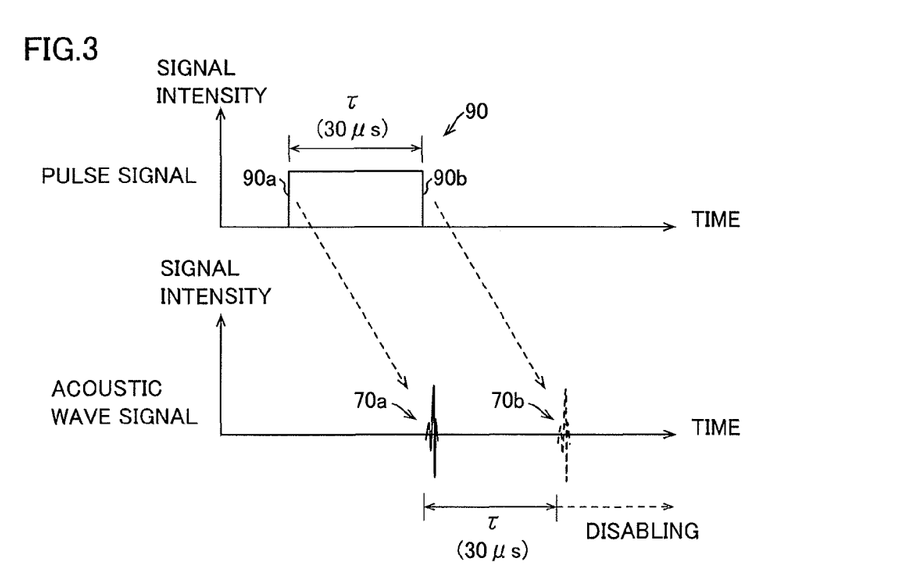
FIG. 3 is a diagram for illustrating processing of an acoustic wave signal in the photoacoustic imaging apparatus according to the first embodiment of the present invention.

According to the first embodiment, a pulse signal 90 of the pulsed light emitted from the LED element 21a or the LED element 21b to the test object 10 is a rectangular wave having a rectangular shape, as shown in FIG. 3. FIG. 3 shows only one pulse signal 90 of a plurality of unshown pulse signals. The pulse signal 90 has a rising edge 90a and a falling edge 90b.

The pulse signal 90 is set to a prescribed pulse width τ (30 μs, for example). The pulse width denotes a time from when the rising edge is 50% of the peak value to when the falling edge is 50% of the peak value. This prescribed pulse width τ is set to a value obtained by the following calculation. In other words, the prescribed pulse width τ is set to a value larger than a time obtained by dividing a detection distance desired by a user by the sound velocity in the test object. As an example of setting the detection distance, the case where the arm of a human body is measured is described. In this case, it is simply required to secure a detection distance corresponding to the thickness of the arm, and hence it is assumed that the detection distance desired by the user is 40 mm. A time obtained by dividing this detection distance of 40 mm by the sound velocity of 1500 m/s in the human body is about 27 μs, and hence 30 μs larger in value than this time is set as the prescribed pulse width τ. If the light absorber 10a exists within the set detection distance, the acoustic wave 70 corresponding to the light absorber 10a is detected, and the light absorber 10a is imaged. The detection distance 40 mm and the prescribed pulse width τ=30 μs corresponding to this are examples of the detection distance and the prescribed pulse width, and the detection distance is varied according to the test object and a measurement site of the test object. Thus, the prescribed pulse width τ is preferably set according to the detection distance desired by the user in each case.

The pulsed light emitted to the test object 10 travels in the test object 10 and is absorbed by the light absorber 10a. As a result of the light absorption, the acoustic wave (see FIG. 2) is generated from the light absorber 10a. At this time, the detecting portion 20 detects two acoustic wave signals from the light absorber 10a in the test object 10 in correspondence to the rising edge 90a and the falling edge 90b of the pulse signal 90. Specifically, the detecting portion 20 detects an acoustic wave signal 70a generated from the light absorber 10a in the test object 10 in correspondence to the rising edge 90a of the pulse signal 90 and an acoustic wave signal 70b (shown by a broken line) generated from the light absorber 10a in the test object 10 in correspondence to the falling edge 90b of the pulse signal 90. After the acoustic wave signal 70a is detected and thereafter a time (30 μs) corresponding to the prescribed pulse width τ elapses, the acoustic wave signal 70b is detected. Then, the signal processing portion 30 acquires the detected acoustic wave signal 70a and acoustic wave signal 70b. Specifically, when the light trigger signal is transmitted and the light source portion 21 emits the pulsed light to the test object 10, the control portion 31 starts to transmit a sampling trigger signal to the A/D converter 34, and the acoustic wave signal detected by the detecting portion 20 and received by the receiving circuit 33 is sampled. The acoustic wave signal 70a is an example of the "first acoustic wave signal" in the present invention. The acoustic wave signal 70b is an example of the "second acoustic wave signal" in the present invention.

According to the first embodiment, the signal processing portion 30 performs processing for disabling the acoustic wave signal 70b of the acquired acoustic wave signal 70a and acoustic wave signal 70b. Specifically, the signal processing portion 30 performs processing for disabling the acoustic wave signal detected after the acoustic wave signal 70a is detected and thereafter the time (30 μs) corresponding to the prescribed pulse width τ elapses. The signal processing portion 30 may perform this processing for disabling the acoustic wave signal by any method including a method for preventing the acoustic wave signal detected after the time corresponding to the prescribed pulse width τ elapses from being sampled and a method for reducing the intensity of the acoustic wave signal detected after the time corresponding to the prescribed pulse width τ elapses to zero. This processing for disabling the acoustic wave signal is performed during a prescribed period from immediately after elapse of the time corresponding to the prescribed pulse width τ until when pulsed light is emitted by a subsequent pulse signal 90. Thus, image information based on the acoustic wave signal 70a can be obtained.

The light source portion 21 continuously emits the pulsed light to the light absorber 10a, and the signal processing portion 30 performs the aforementioned processing, whereby with respect to the subsequent pulse signal, image information based on the acoustic wave signal corresponding to the rising edge can be obtained. On the basis of this image information, the signal processing portion 30 performs processing for imaging the inside of the test object.

A light emission operation is also performed in the same manner on either the LED element 21b or the LED element 21a not first selected, an acoustic wave signal different from the acoustic wave signal of either the LED element 12a or the LED element 21b first selected is acquired and processed, and the signal processing portion 30 performs the processing for imaging the inside of the test object.

According to the first embodiment, a reduction in resolution can be suppressed, and this point is now described with reference to FIGS. 3 and 4.

Figure 4:
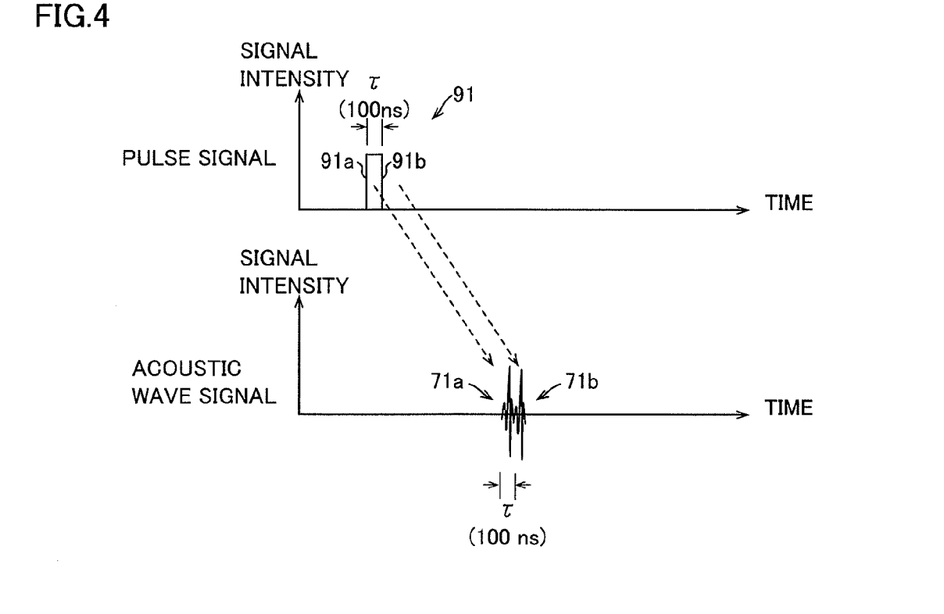
FIG. 4 is a diagram for illustrating a reduction in resolution in a photoacoustic imaging apparatus.

When the prescribed pulse width τ is 100 ns, for example, an acoustic wave signal 71a and an acoustic wave signal 71b are detected by the detecting portion 20 in a state where the acoustic wave signals 71a and 71b partially overlap with each other in correspondence to a pulse signal 91 having a rising edge 91a and a falling edge 91b, as shown in FIG. 4. In this case, the signal processing portion 30 recognizes the acoustic wave signal 71a and the acoustic wave signal 71b as one signal having a time width larger than time widths that the acoustic wave signal 71a and the acoustic wave signal 71b actually have, and hence the actual state of the inside of the test object cannot be faithfully reproduced as an image. Therefore, the resolution is reduced. In FIG. 4, the pulse width is exaggerated for ease of understanding.

When the prescribed pulse width τ is 30 μs, for example, the acoustic wave signal 70a and the acoustic wave signal 70b are detected as different signals by the detecting portion 20, as shown in FIG. 3. In this case, the signal processing portion 30 recognizes the acoustic wave signal 70a and the acoustic wave signal 70b actually generated by the single light absorber 10a as if the same were generated by two separate light absorbers unless any processing is performed, and hence the actual state of the inside of the test object cannot be faithfully reproduced as an image. Therefore, the resolution is reduced.

According to the first embodiment, on the other hand, the signal processing portion 30 performs the processing for disabling the acoustic wave signal 70b of the acquired acoustic wave signal 70a and acoustic wave signal 70b, whereby the acoustic wave signal 70a and the acoustic wave signal 70b do not partially overlap with each other. Thus, the acoustic wave signal 70a and the acoustic wave signal 70b are not recognized as one signal. In addition, the acoustic wave signal 70a and the acoustic wave signal 70b are not recognized as if the same were generated by the separate light absorbers 10a. Therefore, the reduction in resolution can be suppressed.

When the pulse width is smaller than 100 ns, the acoustic wave signal 70a and the acoustic wave signal 70b mostly overlap with each other and are recognized as one signal having a small width, and hence also in this case, the reduction in resolution is suppressed. When the pulse width is at least 100 ns, therefore, the processing for disabling this acoustic wave signal is practically preferably applied. Furthermore, unlike the case where a laser beam source capable of outputting light with an extremely short pulse width is employed, it is difficult to obtain a pulse width smaller than 100 ns when the LED elements are employed as the light source portion, and hence the reduction in resolution can be extremely effectively suppressed by the aforementioned processing.

According to the first embodiment, the following effects can be obtained.

According to the first embodiment, as hereinabove described, the processing for disabling either the acoustic wave signal 70a generated from the light absorber 10a in the test object 10 in correspondence to the rising edge 90a of the pulse signal 90 of the pulsed light or the acoustic wave signal 70b generated from the light absorber 10a in the test object 10 in correspondence to the falling edge 90b of the pulse signal 90 of the pulsed light is performed. Thus, even in the case where the acoustic wave signal 70a and the acoustic wave signal 70b are generated while the peaks thereof are separated from each other by the pulse width $\tau$ when it is difficult to shorten the pulse width $\tau$ of the pulsed light, either the acoustic wave signal 70a or the acoustic wave signal 70b is disabled, whereby the acoustic wave signal 70a and the acoustic wave signal 70b are prevented from partially overlapping with each other and being recognized as one signal having a large width and are prevented from being misidentified as signals generated by the different light absorbers 10a. Thus, the reduction in resolution can be suppressed. Furthermore, imaging processing is performed on the basis of either the acoustic wave signal 70a or the acoustic wave signal 70b, whereby the state of the inside of the test object 10 can be faithfully reproduced as an image on the basis of the acoustic wave signal 70a or the acoustic wave signal 70b.

According to the first embodiment, as hereinabove described, the detecting portion 20 detecting the acoustic wave signal 70a and the acoustic wave signal 70b is provided, and the signal processing portion 30 is configured to perform the imaging processing on the basis of either the acoustic wave signal 70a or the acoustic wave signal 70b by acquiring the acoustic wave signal 70a and the acoustic wave signal 70b detected by the detecting portion 20 and performing the processing for disabling either the acquired acoustic wave signal 70a or acoustic wave signal 70b. Thus, the acoustic wave signal 70a and the acoustic wave signal 70b detected by the detecting portion 20 can be promptly processed by the signal processing portion 30.

According to the first embodiment, as hereinabove described, the LED element 21a and the LED element 21b capable of emitting the pulsed light to the test object 10 is provided in the light source portion 21. Thus, the LED element 21a and the LED element 21b capable of emitting the pulsed light to the test object 10 are employed, whereby power consumption of the light source portion 21 can be reduced unlike the case where a laser beam source is employed as the light source portion 21. In the case where the LED elements (21a and 21b) are employed as a light source as described above, it is currently difficult to shorten the pulse width $\tau$ of the pulsed light in view of the response speed of an LED and the characteristics of a switching element for pulse drive, and hence the present invention is particularly effective.

According to the first embodiment, as hereinabove described, the LED element 21a and the LED element 21b emitting the pulsed light having the first wavelength and the second wavelength different from each other to the test object 10, respectively are provided in the light source portion 21. Furthermore, the signal processing portion 30 is configured to perform the imaging processing on the basis of either the acoustic wave signal 70a or the acoustic wave signal 70b by acquiring the acoustic wave signal 70a and the acoustic wave signal 70b with respect to each of the LED element 21a of the first wavelength and the LED element 21b of the second wavelength and disabling either the acquired acoustic wave signal 70a or acoustic wave signal 70b. Thus, using the LED element 21a of the first wavelength and the LED element 21b of the second wavelength different from the first wavelength, the state of each light absorber 10a in the test object 10 can be faithfully reproduced as an image while the light absorber 10a is determined from the characteristics of the light absorptivity of the light absorber 10a according to the wavelength.

According to the first embodiment, as hereinabove described, the signal processing portion 30 is configured to acquire the acoustic wave signal 70a and the acoustic wave signal 70b separately with respect to each of the LED element 21a of the first wavelength and the LED element 21b of the second wavelength by selecting the LED element 21b of the second wavelength and causing the same to emit after selecting the LED element 21a of the first wavelength and causing the same to emit. Thus, the acoustic wave signal 70a and the acoustic wave signal 70b can be acquired separately with respect to each of the LED element 21a of the first wavelength and the LED element 21b of the second wavelength. Consequently, signal processing on each of the LED element 21a of the first wavelength and the LED element 21b of the second wavelength can be easily performed.

According to the first embodiment, as hereinabove described, the pulsed light emitted by the light source portion 21 has the prescribed pulse width $\tau$, and the prescribed pulse width $\tau$ is rendered larger than the time obtained by dividing the detection distance desired by the user by the sound velocity. Thus, image information (acoustic wave signal) within the detection distance desired by the user can be included during a period from when the acoustic wave signal 70a is detected to when the acoustic wave signal 70b is detected. Therefore, even in the case where the acoustic wave signal 70b detected after the acoustic wave signal 70a is detected and thereafter the time corresponding to the prescribed pulse width $\tau$ elapses is disabled, for example, the reduction in resolution can be suppressed while the image information desired by the user is reliably acquired.

According to the first embodiment, as hereinabove described, the pulsed light emitted by the light source portion 21 has the prescribed pulse width $\tau$, and the signal processing portion 30 is configured to perform the imaging processing on the basis of the acoustic wave signal 70a by disabling the acoustic wave signal 70b detected after the acoustic wave signal 70a is detected and thereafter at least the time corresponding to the prescribed pulse width $\tau$ elapses. Thus, the acoustic wave signal 70b can be easily disabled, utilizing such a time lag of signal detection that after the acoustic wave signal 70a is detected according to the pulsed light emitted by the light source portion 21 and the time corresponding to the prescribed pulse width $\tau$ elapses, the acoustic wave signal 70b is detected without any question.

According to the first embodiment, as hereinabove described, the signal processing portion 30 is configured to perform the processing for disabling the acoustic wave signal 70b during the prescribed period from immediately after the elapse of the time corresponding to the prescribed pulse width τ until when the subsequent pulsed light is emitted. Thus, the processing for disabling the acoustic wave signal 70b acquired in this time's detection period can be reliably terminated by the next time's acoustic wave detection period based on the next time's emission of the pulsed light.

According to the first embodiment, as hereinabove described, in the pulsed light emitted by the light source portion 21, the rising edge 90a where the acoustic wave signal 70a is generated has an inclination equal to or more than the inclination of the falling edge 90b where the acoustic wave signal 70b is generated. Thus, utilizing the property of the acoustic wave signal that the signal intensity of the acoustic wave signal corresponding to the edge of the pulse signal 90 is increased as the inclination of the edge of the pulse signal 90 is increased, the signal intensity of the acoustic wave signal 70a on which the processing for disabling a signal is not performed (which is enabled) can be easily increased.

According to the first embodiment, as hereinabove described, the pulse width of the pulsed light emitted by the light source portion 21 is at least 100 ns. Thus, a waveform in which the acoustic wave signal 70a and the acoustic wave signal 70b partially overlap with each other or a waveform in which the acoustic wave signal 70a and the acoustic wave signal 70b are separated from each other can be easily obtained, and hence the signal processing portion 30 can easily perform the processing for disabling the acoustic wave signal 70b.

According to the first embodiment, as hereinabove described, the detecting portion 20 generating the ultrasonic wave 80 to the test object 10, detecting the ultrasonic wave 80 reflected by the test object 10, and detecting the acoustic wave signal 70a and the acoustic wave signal 70b is provided. Furthermore, the signal processing portion 30 is configured to perform the imaging processing on the basis of the ultrasonic wave 80 and either the acoustic wave signal 70a or the acoustic wave signal 70b detected by the detecting portion 20. Thus, both an image by the ultrasonic wave 80 and an image by the acoustic wave can be obtained, and hence the inside of the test object 10 can be more finely reproduced as an image.

According to the first embodiment, as hereinabove described, the LED element 21a and the LED element 21b capable of emitting the pulsed light to the test object 10, the condensing lens 25 condensing the light from the LED element 21a and the LED element 21b, and the light guide portion 26 guiding the pulsed light condensed by the condensing lens 25 to the vicinity of the test object 10 are provided in the light source portion 21. Thus, even in the case where the LED element 21a and the LED element 21b generating the light easily diffused (easily spread) as compared with a laser beam are employed as a light source, the light from the light source can be reliably emitted to the test object 10.

According to the first embodiment, as hereinabove described, the signal processing portion 30 is configured to start to acquire the acoustic wave signal 70a and the acoustic wave signal 70b when the light source portion 21 emits the pulsed light to the test object 10. Thus, the timing for emitting the pulsed light and the timing for acquiring the acoustic wave signal can be matched, and hence the acoustic wave signal according to the pulsed light can be easily acquired.

According to the first embodiment, as hereinabove described, the light source portion 21 is configured to emit the pulsed light, which is near infrared light, to the test object 10. According to this structure, the near infrared light relatively difficult to absorb in the test object 10 such as a human body, capable of reaching a deep portion of the test object 10, and suitable for measuring a human body or the like can be emitted, and hence the test object 10 such as a human body can be easily measured.

Second Embodiment

A second embodiment is now described with reference to FIGS. 1, 5, and 6. In this second embodiment, either a rising edge 190a or a falling edge 190b of a pulse signal 190 has an inclination larger than the inclination of either the falling edge 190b or the rising edge 190a of the pulse signal 190, unlike the aforementioned first embodiment in which the pulse signal 90 has the rectangular shape.

A photoacoustic imaging apparatus 200 according to the second embodiment of the present invention includes a signal processing portion 130 performing processing for disabling an acoustic wave signal smaller than a prescribed threshold, as shown in FIG. 1. In the second embodiment, portions similar to those in the aforementioned first embodiment shown in FIG. 1 are denoted by the same reference numerals, to omit redundant description.

Figure 5:
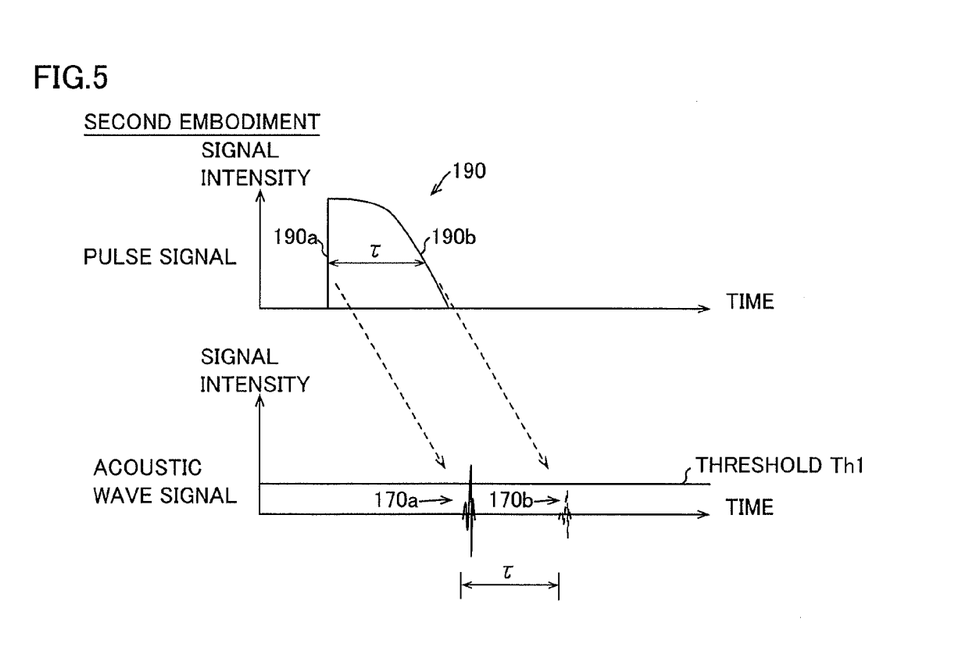
FIG. 5 is a diagram for illustrating processing of an acoustic wave signal in the case where the inclination of a falling edge of a pulse signal is gentle according to a second embodiment of the present invention.
Figure 6:
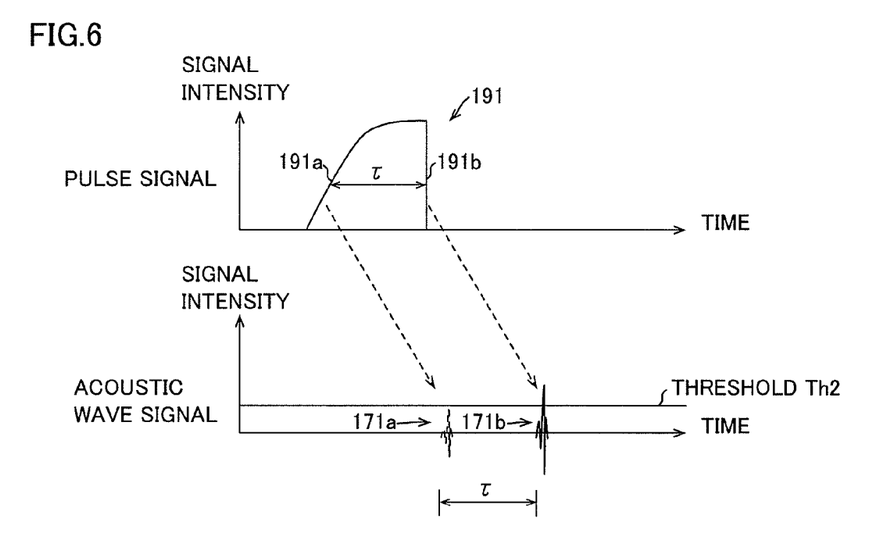
FIG. 6 is a diagram for illustrating processing of an acoustic wave signal in the case where the inclination of a rising edge of a pulse signal is gentle according to the second embodiment of the present invention.

According to the second embodiment, the pulse signal 190 of pulsed light emitted to a light absorber 10a by a light source portion 21 has the rising edge 190a rising vertically, as shown in FIG. 5. The pulse signal 190 also has the falling edge 190b falling gently. In other words, the rising edge 190a has the inclination larger than the inclination of the falling edge 190b in the pulse signal 190. The pulse signal 190 has a prescribed pulse width τ.

According to the second embodiment, a detecting portion 20 (see FIG. 1) detects an acoustic wave signal 170a corresponding to the rising edge 190a and an acoustic wave signal 170b corresponding to the falling edge 190b. The intensity of the acoustic wave signal changes according to the time change of the pulse signal, and hence the acoustic wave signal 170a corresponding to the rising edge 190a whose time change is sharp is detected with larger signal intensity than the acoustic wave signal 170b corresponding to the falling edge 190b whose time change is slow. The acoustic wave signal 170a is an example of the "first acoustic wave signal" in the present invention. The acoustic wave signal 170b is an example of the "second acoustic wave signal" in the present invention.

According to the second embodiment, the signal processing portion 130 performs the processing for disabling the acoustic wave signal 170b smaller than the prescribed threshold Th1. The signal processing portion 130 may perform this processing for disabling the acoustic wave signal by any method including a method for preventing the acoustic wave signal smaller than the prescribed threshold Th1 from being sampled and a method for reducing the intensity of the acoustic wave signal smaller than the prescribed threshold Th1 to zero, for example. Thus, image information based on the acoustic wave signal 170a can be obtained.

The prescribed threshold Th1 is a value smaller than the maximum signal intensity of the acoustic wave signal 170a and larger than the maximum signal intensity of the acoustic wave signal 170b. The prescribed threshold Th1 may have a prescribed proportion to the maximum signal intensity of the acoustic wave signal 170a or may be determined by another method, for example.

A pulse signal 191 having a rising edge 191a rising gently and a falling edge 191b falling vertically contrary to FIG. 5 is now described with reference to FIG. 6.

Also in this case, the intensity of an acoustic wave signal changes according to the time change of the pulse signal, similarly to the case of FIG. 5, and hence an acoustic wave signal 171b corresponding to the rising edge 191b whose time change is sharp is detected with larger signal intensity than an acoustic wave signal 171a corresponding to the falling edge 191a whose time change is slow. The acoustic wave signal 171a is an example of the "first acoustic wave signal" in the present invention. The acoustic wave signal 171b is an example of the "second acoustic wave signal" in the present invention.

The signal processing portion 130 performs processing for disabling the acoustic wave signal 171a smaller than a prescribed threshold Th2. Thus, image information based on the acoustic wave signal 171b can be obtained. The prescribed threshold Th2 is a value smaller than the maximum signal intensity of the acoustic wave signal 171b and larger than the maximum signal intensity of the acoustic wave signal 171a.

According to this processing for disabling the acoustic wave signal in the second embodiment, the signal processing portion 130 can also perform processing for distinguishing the acoustic wave signals 170a (171a) and 170b (171b) from each other and disabling either the acoustic wave signal 170a (171a) or 170b (171b) not only in the case where the pulse width τ is at least 100 ns but also in the case where the pulse width is smaller than 100 ns, unlike the first embodiment.

The remaining structure of the photoacoustic imaging apparatus 200 according to the second embodiment is similar to that of the photoacoustic imaging apparatus 100 according to the aforementioned first embodiment.

According to the second embodiment, the following effects can be obtained.

According to the second embodiment, as hereinabove described, in the pulsed light emitted by the light source portion 21, either the rising edge 190a (191a) or the falling edge 190b (191b) has the inclination larger than the inclination of either the falling edge 190b (191b) or the rising edge 190a (191a), and the signal processing portion 130 is configured to perform imaging processing on the basis of either the acoustic wave signal 170a (171a) or the acoustic wave signal 170b (171b) by disabling the acoustic wave signal 170a (171a) or the acoustic wave signal 170b (171b) having signal intensity smaller than the prescribed threshold Th1 (Th2) that is the value smaller than the signal intensity of the acoustic wave signal 170a (171a) or the acoustic wave signal 170b (171b) corresponding to either the rising edge 190a (191a) or the falling edge 190b (191b). Thus, utilizing the property of the acoustic wave signal that the signal intensity of the acoustic wave signal corresponding to the edge of the pulse signal 190 is increased as the inclination of the edge of the pulse signal 190 is increased, the acoustic wave signals 170a (171a) and 170b (171b) can be distinguished from each other with the prescribed threshold Th1 (Th2), and hence the acoustic wave signal 171a or the acoustic wave signal 170b can be reliably disabled.

According to the second embodiment, as hereinabove described, the light source portion 21 emits the pulsed light such that the rising edge 190a having the inclination larger than that of the falling edge 190b rises substantially vertically or the falling edge 191b having the inclination larger than that of the rising edge 191a falls substantially vertically. Thus, on the rising edge 190a or the falling edge 191b where the enabled acoustic wave signal is generated, the inclination can be substantially maximized, and hence the intensity of the enabled signal can be reliably increased.

According to the second embodiment, as hereinabove described, the prescribed threshold Th1 (Th2) is the value smaller than the signal intensity of the acoustic wave signal 170a or the acoustic wave signal 171b corresponding to either the rising edge 190a or the falling edge 191b and larger than the signal intensity of the acoustic wave signal 170b or the acoustic wave signal 171a corresponding to either the falling edge 191b or the rising edge 190a. Thus, the acoustic wave signal 170a (171a) and the acoustic wave signal 170b (171b) can be more reliably distinguished from each other with the prescribed threshold Th1 (Th2), and the acoustic wave signal 171a or the acoustic wave signal 170b can be more reliably disabled.

The remaining effects of the second embodiment are similar to those of the aforementioned first embodiment.

Third Embodiment

A third embodiment is now described with reference to FIGS. 1 and 7. In this third embodiment, a signal processing portion 230 performs imaging processing with both an acoustic wave signal 270a and an acoustic wave signal 270b, unlike each of the aforementioned first and second embodiments in which the signal processing portion 30 (130) performs the imaging processing with only one of the acoustic wave signal 70a (170a, 171a) and the acoustic wave signal 70b (170b, 171b). The acoustic wave signal 270a is an example of the "first acoustic wave signal" in the present invention. The acoustic wave signal 270b is an example of the "second acoustic wave signal" in the present invention.

A photoacoustic imaging apparatus 300 according to the third embodiment of the present invention includes the signal processing portion 230 acquiring first image forming information based on the acoustic wave signal 270a (see FIG. 7) and second image forming information based on the acoustic wave signal 270b (see FIG. 7), as shown in FIG. 1.

Figure 7:
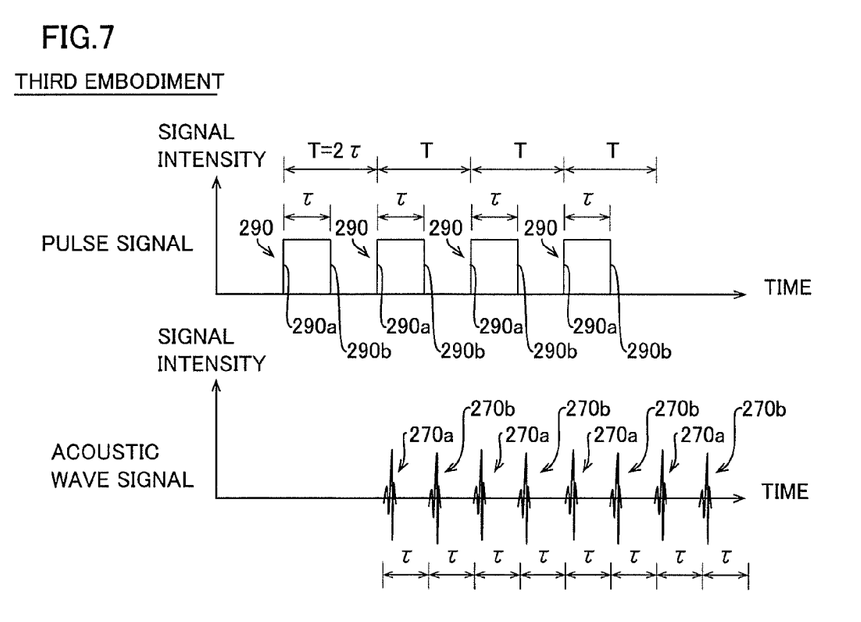
FIG. 7 is a diagram for illustrating processing of an acoustic wave signal in a photoacoustic imaging apparatus according to a third embodiment of the present invention.

According to the third embodiment, the duty ratio of a pulse signal 290 of pulsed light emitted to a light absorber 10a by a light source portion 21 is 50%, as shown in FIG. 7. In other words, the time of the prescribed pulse width τ of the pulse signal 290 is 50% of the time of a cycle T. In the pulse signal 290, the inclinations (time changes) of a rising edge 290a and a falling edge 290b are equal to each other in magnitude. The pulse width denotes a time from when the rising edge is 50% of the peak value to when the falling edge is 50% of the peak value. The cycle denotes a time obtained by summing the duration of the ON-state and the OFF-state of one pulse signal.

FIG. 7 shows four pulse signals 290. A detecting portion 20 detects acoustic wave signals 270a and acoustic wave signals 270b in correspondence to rising edges 290a and falling edges 290b of these four pulse signals. At this time, the acoustic wave signals 270a and the acoustic wave signals 270b adjacent to each other are detected at equal time intervals. In other words, the acoustic wave signals 270a and the acoustic wave signals 270b adjacent to each other are separated by a time corresponding to the prescribed pulse width τ and are detected. This prescribed pulse width τ is set to a value obtained by the following calculation. In other words, the prescribed pulse width τ is set to a value larger than a time obtained by dividing a detection distance desired by a user by the sound velocity in a test object. As an example of setting the detection distance, the case where the arm of a human body is measured is described. In this case, it is simply required to secure a detection distance corresponding to the thickness of the arm, and hence it is assumed that the detection distance desired by the user is 40 mm. A time obtained by dividing this detection distance of 40 mm by the sound velocity of 1500 m/s in the human body is about 27 μs, and hence 30 μs larger in value than this time is set as the prescribed pulse width τ. If the light absorber 10a exists within the set detection distance, an acoustic wave 70 corresponding to the light absorber 10a is detected, and the light absorber 10a is imaged. The detection distance 40 mm and the prescribed pulse width τ=30 μs corresponding to this are examples of the detection distance and the prescribed pulse width, and the detection distance is varied according to the test object and a measurement site of the test object. Thus, the prescribed pulse width τ is preferably set according to the detection distance desired by the user in each case.

According to the third embodiment, the signal processing portion 230 acquires two acoustic wave signals 270a and 270b as separate image information with respect to one pulse signal 290. The acoustic wave signal 270a and the acoustic wave signal 270b are signals based on an acoustic wave generated from one light absorber 10a (see FIG. 2) due to one pulse signal 290. Therefore, the acoustic wave signal 270a and the acoustic wave signal 270b are acquired as separate image information, whereby two pieces of image information can be obtained from one pulsed light. The signal processing portion 230 performs the imaging processing on the basis of the acoustic wave signal 270a and the acoustic wave signal 270b acquired separately.

The remaining structure of the photoacoustic imaging apparatus 300 according to the third embodiment is similar to that of the photoacoustic imaging apparatus 100 according to the aforementioned first embodiment.

According to the third embodiment, the following effects can be obtained.

According to the third embodiment, as hereinabove described, the signal processing portion 230 separately acquiring the acoustic wave signal 270a generated from the light absorber 10a in a test object 10 in correspondence to the rising edge 290a of the pulse signal 290 of the pulsed light and the acoustic wave signal 270b generated from the light absorber 10a in the test object 10 in correspondence to the falling edge 290b of the pulse signal 290 of the pulsed light and performing the imaging processing on the basis of the acoustic wave signal 270a and the acoustic wave signal 270b separately acquired is provided. Thus, the two pieces of image information (the acoustic wave signal 270a and the acoustic wave signal 270b) can be obtained from one pulse signal 290, and hence a double amount of image information (a double amount of sampling information) can be obtained as compared with the case where one piece of image information is obtained from one pulse signal 290.

According to the third embodiment, as hereinabove described, the pulsed light emitted by the light source portion 21 has the rising edge 290a and the falling edge 290b whose inclinations are substantially equal to each other in magnitude. Thus, the intensity of the acoustic wave signal 270a and the intensity of the acoustic wave signal 270b can be rendered substantially equal to each other, and hence the signal processing portion 230 can easily perform the imaging processing based on the acoustic wave signal 270a and the acoustic wave signal 270b.

According to the third embodiment, as hereinabove described, the pulsed light emitted by the light source portion 21 has a substantially rectangular shape. Thus, on both the rising edge 290a and the falling edge 290b, the inclination can be substantially maximized, and hence the intensity of both the acoustic wave signal 270a and the acoustic wave signal 270b can be reliably increased.

The remaining effects of the third embodiment are similar to those of the aforementioned first embodiment.

The embodiments disclosed this time must be considered as illustrative in all points and not restrictive. The range of the present invention is shown not by the above description of the embodiments but by the scope of claims for patent, and all modifications within the meaning and range equivalent to the scope of claims for patent are further included.

For example, while the light source portion 21 emits the near infrared light to the test object 10 in each of the aforementioned first to third embodiments, the present invention is not restricted to this. According to the present invention, the light source portion 21 may alternatively emit light of a wavelength other than the near infrared light to the test object 10.

While the light source portion 21 has the LED element 21a and the LED element 21b in each of the aforementioned first to third embodiments, the present invention is not restricted to this. According to the present invention, a laser beam source capable of emitting light having a prescribed wavelength may alternatively be applied as the light source portion. In this case, a pulsed laser beam having a pulse width of at least 100 ns is preferably employed when the first or third embodiment is applied.

While the light source portion 21 has the LED element 21a and the LED element 21b capable of emitting the light having the wavelengths different from each other in each of the aforementioned first to third embodiments, the present invention is not restricted to this. According to the present invention, the light source portion 21 may alternatively have only the LED element of one wavelength.

While the photoacoustic imaging apparatus 100 (200, 300) includes the detecting portion 20 in each of the aforementioned first to third embodiments, the present invention is not restricted to this. According to the present invention, the photoacoustic imaging apparatus may not include the detecting portion. For example, a detecting apparatus separate from the photoacoustic imaging apparatus may detect the acoustic wave signal, and data of the acoustic wave signal detected by this detecting apparatus may be input into the photoacoustic imaging apparatus, whereby the imaging processing may be performed.

While the signal processing portion 30 performs the processing for disabling the acoustic wave signal 70b corresponding to the falling edge 90b of the pulse signal 90 in the aforementioned first embodiment, the present invention is not restricted to this. According to the present invention, the signal processing portion may alternatively perform processing for disabling the acoustic wave signal 70a corresponding to the rising edge 90a of the pulse signal 90.

While the prescribed pulse width τ is set to be larger than the time obtained by dividing the detection distance desired by the user by the sound velocity in the aforementioned first embodiment, the present invention is not restricted to this. According to the present invention, the prescribed pulse width τ may alternatively be set to be equal to or less than the time obtained by dividing the detection distance desired by the user by the sound velocity.

While the pulse signal 90 has the rectangular shape in the aforementioned first embodiment, the present invention is not restricted to this. According to the present invention, the pulse signal may alternatively have a waveform other than the rectangular shape. The pulse signal may have a waveform of a sine wave, a triangular wave, a saw-tooth wave, or the like, for example.

What is claimed is:

1. A photoacoustic imaging apparatus comprising:
   a light source portion emitting pulsed light to a test object; and
   a signal processing portion performing imaging processing on the basis of either a first acoustic wave signal or a second acoustic wave signal by performing processing for disabling either the first acoustic wave signal generated from a detection target in the test object in correspondence to a rising edge of a pulse signal of the pulsed light or the second acoustic wave signal generated from the detection target in the test object in correspondence to a falling edge of the pulse signal of the pulsed light according to the pulsed light emitted by the light source portion.

2. The photoacoustic imaging apparatus according to claim 1, further comprising a detecting portion detecting the first acoustic wave signal and the second acoustic wave signal, wherein
   the signal processing portion is configured to acquire the first acoustic wave signal and the second acoustic wave signal detected by the detecting portion and perform the imaging processing on the basis of either the first acoustic wave signal or the second acoustic wave signal by performing the processing for disabling either the first acoustic wave signal or the second acoustic wave signal which has been acquired.

3. The photoacoustic imaging apparatus according to claim 1, wherein
   the light source portion includes an LED element emitting the pulsed light to the test object.

4. The photoacoustic imaging apparatus according to claim 1, wherein
   the light source portion includes LED elements emitting the pulsed light having a first wavelength and a second wavelength different from each other to the test object, and
   the signal processing portion is configured to acquire the first acoustic wave signal and the second acoustic wave signal with respect to each of the LED elements of the first wavelength and the second wavelength and perform the imaging processing on the basis of either the first acoustic wave signal or the second acoustic wave signal by performing the processing for disabling either the first acoustic wave signal or the second acoustic wave signal which has been acquired.

5. The photoacoustic imaging apparatus according to claim 4, wherein
   the signal processing portion is configured to acquire the first acoustic wave signal and the second acoustic wave signal separately with respect to each of the LED elements of the first wavelength and the second wavelength by selecting the LED element of the second wavelength and causing the same to emit after selecting the LED element of the first wavelength and causing the same to emit.

6. The photoacoustic imaging apparatus according to claim 1, wherein
   the pulsed light emitted by the light source portion has a prescribed pulse width, and
   the prescribed pulse width is larger than a time obtained by dividing a detection distance desired by a user by a sound velocity.

7. The photoacoustic imaging apparatus according to claim 1, wherein
   the pulsed light emitted by the light source portion has a prescribed pulse width, and
   the signal processing portion is configured to perform the imaging processing on the basis of the first acoustic wave signal by disabling the second acoustic wave signal detected after the first acoustic wave signal is detected and thereafter at least a time corresponding to the prescribed pulse width elapses.

8. The photoacoustic imaging apparatus according to claim 7, wherein
   the signal processing portion is configured to perform processing for disabling the second acoustic wave signal during a prescribed period from immediately after elapse of the time corresponding to the prescribed pulse width until when subsequent pulsed light is emitted.

9. The photoacoustic imaging apparatus according to claim 7, wherein
   in the pulsed light emitted by the light source portion, the rising edge where the first acoustic wave signal is generated has an inclination equal to or more than an inclination of the falling edge where the second acoustic wave signal is generated.

10. The photoacoustic imaging apparatus according to claim 1, wherein
    in the pulsed light emitted by the light source portion, either the rising edge or the falling edge has an inclination larger than an inclination of either the falling edge or the rising edge, and
    the signal processing portion is configured to perform the imaging processing on the basis of either the first acoustic wave signal or the second acoustic wave signal by disabling the first acoustic wave signal or the second acoustic wave signal having signal intensity smaller than a prescribed threshold that is a value smaller than signal intensity of the first acoustic wave signal or the second acoustic wave signal corresponding to either the rising edge or the falling edge.

11. The photoacoustic imaging apparatus according to claim 10, wherein
    in the pulsed light emitted by the light source portion, either the rising edge or the falling edge having the inclination larger than the inclination of either the falling edge or the rising edge substantially vertically rises or falls.

12. The photoacoustic imaging apparatus according to claim 10, wherein
    the prescribed threshold is a value smaller than the signal intensity of the first acoustic wave signal or the second acoustic wave signal corresponding to either the rising edge or the falling edge and larger than signal intensity of the second acoustic wave signal or the first acoustic wave signal corresponding to either the falling edge or the rising edge.

13. The photoacoustic imaging apparatus according to claim 1, wherein
    a pulse width of the pulsed light emitted by the light source portion is at least 100 ns.

14. The photoacoustic imaging apparatus according to claim 1, further comprising a detecting portion generating an ultrasonic wave to the test object, detecting the ultrasonic wave reflected by the test object, and detecting the first acoustic wave signal and the second acoustic wave signal, wherein the signal processing portion is configured to perform the imaging processing on the basis of the ultrasonic wave detected by the detecting portion and either the first acoustic wave signal or the second acoustic wave signal.

15. The photoacoustic imaging apparatus according to claim 1, wherein the light source portion includes an LED element configured to emit the pulsed light to the test object, a condensing lens condensing the pulsed light from the LED element, and a light guide portion guiding the pulsed light condensed by the condensing lens to a vicinity of the test object.

16. The photoacoustic imaging apparatus according to claim 1, wherein the signal processing portion is configured to start to acquire the first acoustic wave signal and the second acoustic wave signal when the light source portion emits the pulsed light to the test object.

17. The photoacoustic imaging apparatus according to claim 1, wherein the light source portion is configured to emit the pulsed light, which is near infrared light, to the test object.

18. A photoacoustic imaging apparatus comprising:

a light source portion configured to emit pulsed light to a test object such that a duty ratio is 50%, and a signal processing portion separately acquiring a first acoustic wave signal generated from a detection target in the test object in correspondence to a rising edge of a pulse signal of the pulsed light and a second acoustic wave signal generated from the detection target in the test object in correspondence to a falling edge of the pulse signal of the pulsed light according to the pulsed light emitted by the light source portion and performing imaging processing on the basis of the first acoustic wave signal and the second acoustic wave signal which have been separately acquired.

19. The photoacoustic imaging apparatus according to claim 18, wherein in the pulsed light emitted by the light source portion, an inclination of the rising edge and an inclination of the falling edge are substantially equal to each other in magnitude.

20. The photoacoustic imaging apparatus according to claim 18, wherein the pulsed light emitted by the light source portion has a substantially rectangular shape.

* * * * *